(12) United States Patent
Kawata

(10) Patent No.: US 12,219,785 B2
(45) Date of Patent: Feb. 4, 2025

(54) DETECTION DEVICE

(71) Applicant: Japan Display Inc., Tokyo (JP)

(72) Inventor: Yasushi Kawata, Tokyo (JP)

(73) Assignee: JAPAN DISPLAY INC., Tokyo (JP)

( * ) Notice: Subject to any disclaimer, the term of this patent is extended or adjusted under 35 U.S.C. 154(b) by 402 days.

(21) Appl. No.: 17/696,291

(22) Filed: Mar. 16, 2022

(65) Prior Publication Data

US 2022/0208858 A1 Jun. 30, 2022

Related U.S. Application Data

(63) Continuation of application No. PCT/JP2020/031707, filed on Aug. 21, 2020.

(30) Foreign Application Priority Data

Sep. 19, 2019 (JP) ................. 2019-170457

(51) Int. Cl.
H01L 27/30 (2006.01)
G06V 40/13 (2022.01)
H10K 39/32 (2023.01)

(52) U.S. Cl.
CPC ......... *H10K 39/32* (2023.02); *G06V 40/1318* (2022.01)

(58) Field of Classification Search
CPC .... H10K 39/32; H10K 30/30; G06V 40/1318; G06V 40/1382; Y02E 10/549; A61B 5/1171; A61B 5/1172; H01L 27/146; H01L 31/10; H04N 25/70
See application file for complete search history.

(56) References Cited

U.S. PATENT DOCUMENTS

| 10,605,678 | B2 | 3/2020 | Kihara et al. |
| 2013/0206993 | A1 | 8/2013 | Ibuki et al. |
| 2017/0170238 | A1 | 6/2017 | Lee et al. |
| 2018/0219045 | A1 | 8/2018 | Murata et al. |
| 2018/0277604 | A1 | 9/2018 | Joei |
| 2019/0181183 | A1 | 6/2019 | Lee et al. |
| 2020/0111841 | A1 | 4/2020 | Lee et al. |
| 2020/0119100 | A1 | 4/2020 | Murata et al. |

FOREIGN PATENT DOCUMENTS

| JP | 2008209559 | A | 9/2008 |
| JP | 2011249623 | A | 12/2011 |
| JP | 2013165109 | A | 8/2013 |
| JP | 2017112376 | A | 6/2017 |
| WO | 2017014146 | A1 | 1/2017 |
| WO | 2017061176 | A1 | 4/2017 |

OTHER PUBLICATIONS

Synthetic Metals vol. 253, Jul. 2019, pp. 40-47 (Year: 2019).*
Japanese Office Action issued on Apr. 4, 2023 in corresponding Japanese Application No. 2019-170457.
Search Report issued in International Patent Application No. PCT/JP2020/031707 on Oct. 27, 2020.

* cited by examiner

*Primary Examiner* — Jarrett J Stark
(74) *Attorney, Agent, or Firm* — K&L Gates LLP

(57) ABSTRACT

According to an aspect, a detection device includes: a substrate; an anode electrode provided on the substrate; a cathode electrode that is provided on the same layer as that of the anode electrode and is adjacent to the anode electrode; and an organic semiconductor layer that has a structure in which a p-type semiconductor layer and an n-type semiconductor layer coexist and that is provided so as to cover the anode electrode and the cathode electrode.

6 Claims, 8 Drawing Sheets

DETECTION DEVICE

CROSS-REFERENCE TO RELATED APPLICATION

This application claims the benefit of priority from Japanese Patent Application No. 2019-170457 filed on Sep. 19, 2019 and International Patent Application No. PCT/JP2020/031707 filed on Aug. 21, 2020, the entire contents of which are incorporated herein by reference.

BACKGROUND

1. Technical Field

What is disclosed herein relates to a detection device.

2. Description of the Related Art

In these years, optical biosensors are known as biosensors used, for example, for personal authentication. For example, fingerprint sensors and vein sensors are known as such biosensors. An optical biosensor includes a photoelectric conversion element such as a photodiode, and the photoelectric conversion element changes an output signal thereof depending on an amount of irradiating light. In Japanese Patent Application Laid-open Publication No. 2017-112376 (JP-A-2017-112376), an organic photoelectric layer including an organic semiconductor is used as the photoelectric conversion element. In JP-A-2017-112376, the organic photoelectric layer and an upper transparent electrode layer are provided in this order on a lower transparent electrode layer.

In JP-A-2017-112376, since the upper transparent electrode layer is provided on the organic photoelectric layer, the organic photoelectric layer may be damaged in a process of forming the upper transparent electrode layer. Therefore, when the configuration of JP-A-2017-112376 is applied to an optical biosensor, characteristics of the sensor element may deteriorate.

SUMMARY

According to an aspect, a detection device includes: a substrate; an anode electrode provided on the substrate; a cathode electrode that is provided on the same layer as that of the anode electrode and is adjacent to the anode electrode; and an organic semiconductor layer that has a structure in which a p-type semiconductor layer and an n-type semiconductor layer coexist and that is provided so as to cover the anode electrode and the cathode electrode.

DETAILED DESCRIPTION

Figure 1:
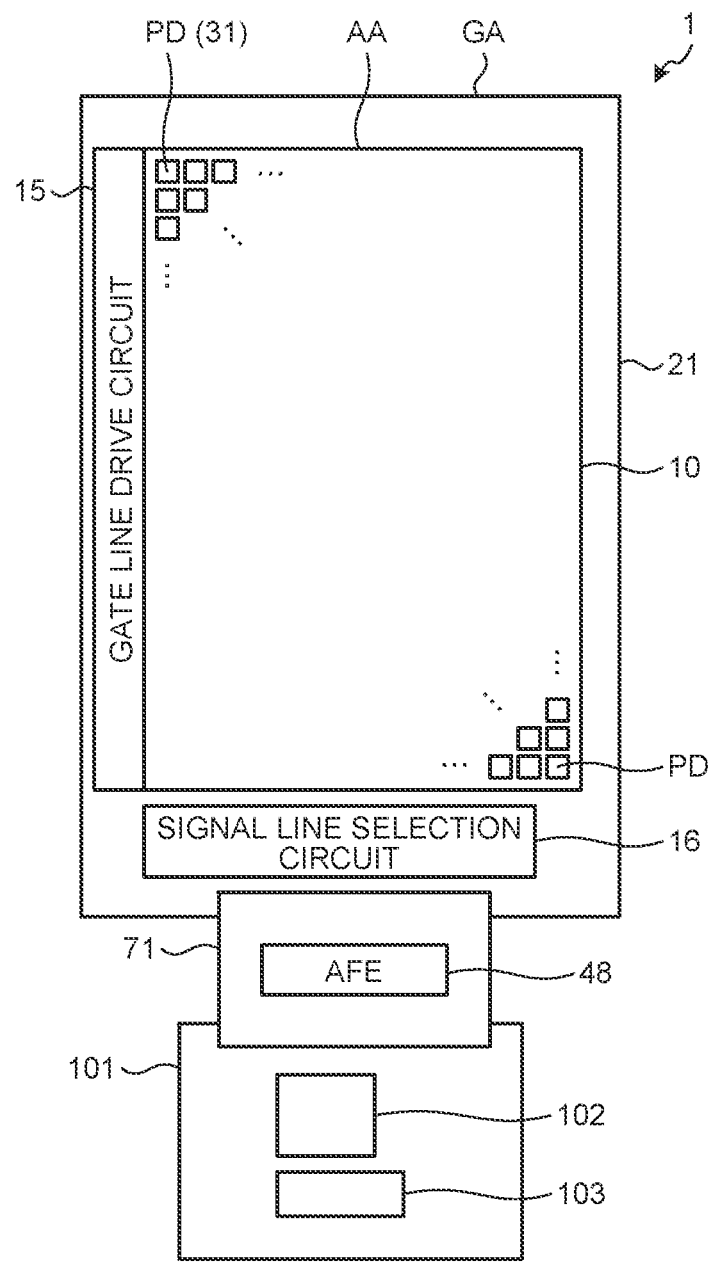
FIG. 1 is a plan view illustrating a detection device according to a first embodiment.

The following describes modes (embodiments) for carrying out the present disclosure in detail with reference to the drawings. The present disclosure is not limited to the description of the embodiments given below. Components described below include those easily conceivable by those skilled in the art or those substantially identical thereto. In addition, the components described below can be combined as appropriate. What is disclosed herein is merely an example, and the present disclosure naturally encompasses appropriate modifications easily conceivable by those skilled in the art while maintaining the gist of the disclosure. To further clarify the description, the drawings schematically illustrate, for example, widths, thicknesses, and shapes of various parts as compared with actual aspects thereof, in some cases. However, they are merely examples, and interpretation of the present disclosure is not limited thereto. The same component as that described with reference to an already mentioned drawing is denoted by the same reference numeral through the description and the drawings, and detailed description thereof may not be repeated where appropriate.

In this disclosure, when an element is described as being "on" another element, the element can be directly on the other element, or there can be one or more elements between the element and the other element.

First Embodiment

FIG. 1 is a plan view illustrating a detection device according to a first embodiment. As illustrated in FIG. 1, a detection device 1 includes an insulating substrate 21, a sensor 10, a gate line drive circuit 15, a signal line selection circuit 16, a detection circuit 48, a control circuit 102, and a power supply circuit 103.

A control board 101 is electrically coupled to the insulating substrate 21 through a flexible printed circuit board 71. The flexible printed circuit board 71 is provided with the detection circuit 48. The control board 101 is provided with the control circuit 102 and the power supply circuit 103. The control circuit 102 is, for example, a field-programmable gate array (FPGA). The control circuit 102 supplies control signals to the sensor 10, the gate line drive circuit 15, and the signal line selection circuit 16 to control a detection operation of the sensor 10. The power supply circuit 103 supplies voltage signals including a power supply signal SVS (refer to FIG. 4) to the sensor 10 and the gate line drive circuit 15.

The insulating substrate 21 has a detection area AA and a peripheral area GA. The detection area AA is an area overlapping a plurality of photoelectric conversion elements PD (photodiodes) included in the sensor 10. The peripheral area GA is an area outside the detection area AA, and is an area not overlapping the photoelectric conversion elements PD. The gate line drive circuit 15 and the signal line selection circuit 16 are provided in the peripheral area GA.

The sensor 10 is a photosensor that includes the photoelectric conversion elements PD. The photoelectric conversion elements PD are arranged in a matrix having a row-column configuration in the detection area AA of the insulating substrate 21. The photoelectric conversion elements PD of the sensor 10 are photodiodes, and each include an organic semiconductor layer 31, a plurality of anode electrodes 35, and a plurality of cathode electrodes 36 (refer to FIG. 5). Each of the photoelectric conversion elements PD outputs an electrical signal corresponding to light irradiating the photoelectric conversion element PD. The detection device 1 detects information on a living body based on detection signals Vdet received from the photoelectric conversion elements PD. A specific configuration example of the photoelectric conversion elements PD will be described later.

Figure 2:
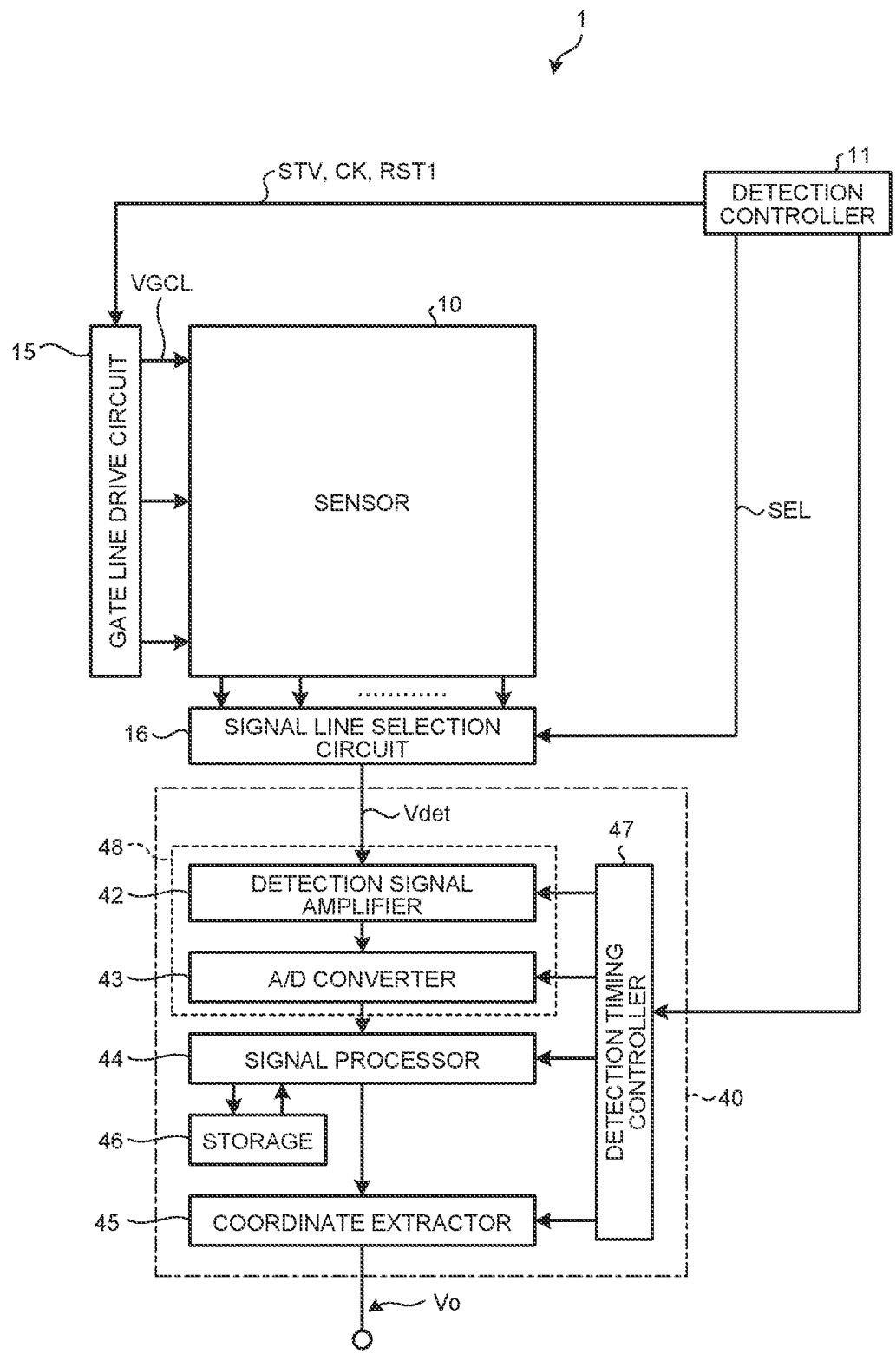
FIG. 2 is a block diagram illustrating a configuration example of the detection device according to the first embodiment.

FIG. 2 is a block diagram illustrating a configuration example of the detection device according to the first embodiment. As illustrated in FIG. 2, the detection device 1 further includes a detection controller 11 and a detector 40. The control circuit 102 includes one, some, or all functions of the detection controller 11. The control circuit 102 also includes one, some, or all functions of the detector 40. In FIG. 1, the detection circuit 48 is provided on the flexible printed circuit board 71 but may be built into the control circuit 102.

Each of the photoelectric conversion elements PD of the sensor 10 outputs the electrical signal corresponding to the light irradiating the photoelectric conversion element PD as a corresponding one of the detection signals Vdet to the signal line selection circuit 16. The sensor 10 performs the detection in response to a gate drive signal VGCL supplied from the gate line drive circuit 15.

The detection controller 11 is a circuit that supplies respective control signals to the gate line drive circuit 15, the signal line selection circuit 16, and the detector 40 to control operations thereof. The detection controller 11 supplies various control signals including a start signal STV, a clock signal CK, and a reset signal RST1 to the gate line drive circuit 15. The detection controller 11 also supplies various control signals including a selection signal SEL to the signal line selection circuit 16.

The gate line drive circuit 15 drives a plurality of gate lines GCL (refer to FIG. 3) based on the various control signals. The gate line drive circuit 15 sequentially or simultaneously selects the gate lines GCL and supplies the gate drive signals VGCL to the selected gate lines GCL. Through this operation, the gate line drive circuit 15 selects the photoelectric conversion elements PD coupled to the gate lines GCL.

Figure 3:
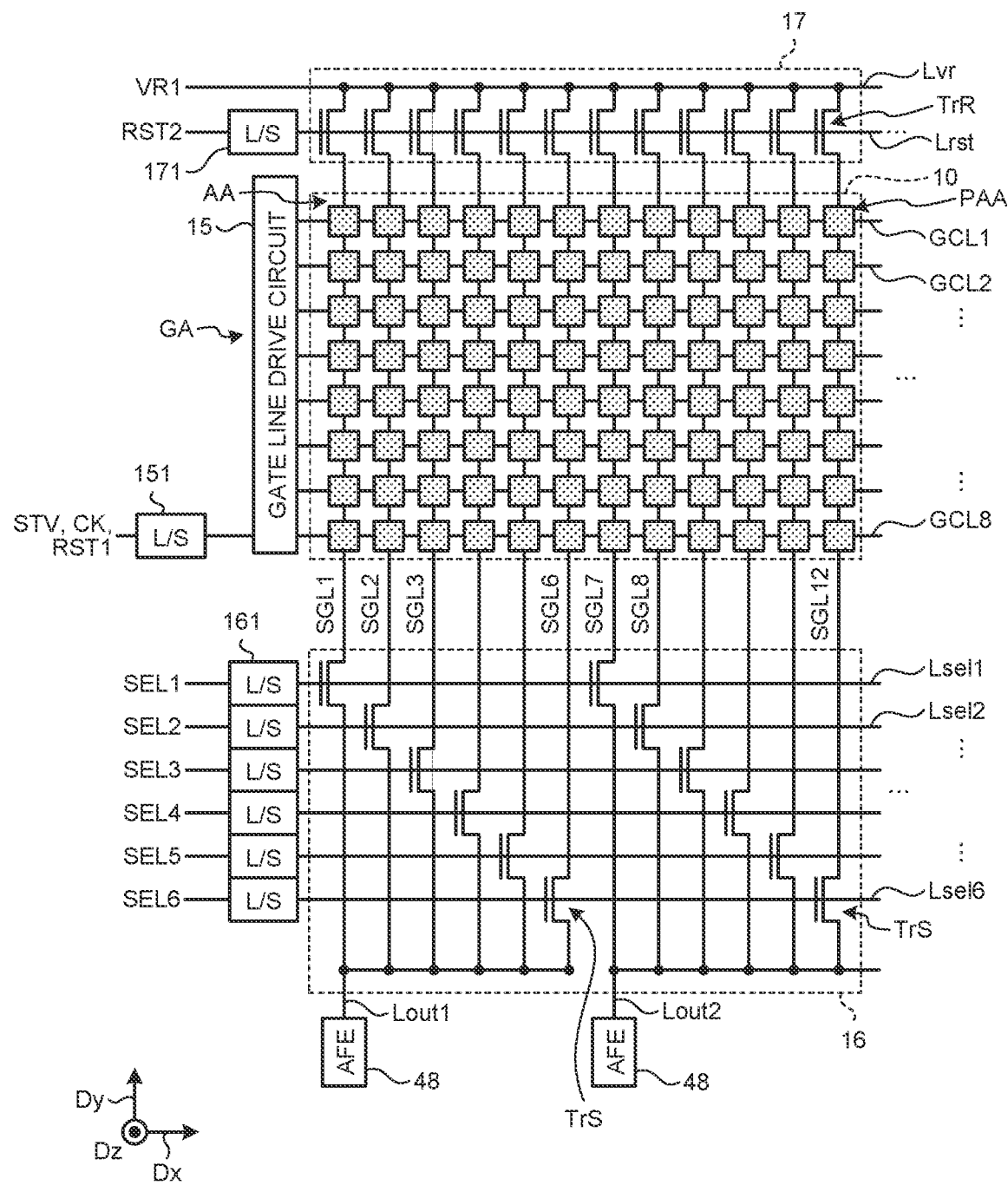
FIG. 3 is a circuit diagram illustrating the detection device.

The signal line selection circuit 16 is a switch circuit that sequentially or simultaneously selects a plurality of signal lines SGL (refer to FIG. 3). The signal line selection circuit 16 couples the selected signal lines SGL to the detection circuit 48 based on the selection signal SEL supplied from the detection controller 11. By this operation, the signal line selection circuit 16 outputs the detection signals Vdet of the photoelectric conversion elements PD to the detector 40.

The detector 40 includes the detection circuit 48, a signal processor 44, a coordinate extractor 45, a storage 46, and a detection timing controller 47. Based on a control signal supplied from the detection controller 11, the detection timing controller 47 controls the detection circuit 48, the signal processor 44, and the coordinate extractor 45 such that they operate in synchronization with one another.

The detection circuit 48 is, for example, an analog front-end (AFE) circuit. The detection circuit 48 is a signal processing circuit having functions of at least a detection signal amplifier 42 and an analog-to-digital (A/D) converter 43. The detection signal amplifier 42 amplifies the first detection signals Vdet. The A/D converter 43 converts analog signals output from the detection signal amplifier 42 into digital signals.

The signal processor 44 is a logic circuit that detects, based on an output signal of the detection circuit 48, a predetermined physical quantity received by the sensor 10. When a finger Fg is in contact with or in proximity to a detection surface, the signal processor 44 can detect asperities on a surface of the finger Fg or a palm based on the signal from the detection circuit 48. The signal processor 44 can also detect the information on the living body based on the signal from the detection circuit 48. Examples of the information on the living body include a blood vessel image, a pulse wave, pulsation, and a blood oxygen saturation level of the finger Fg or the palm.

The storage 46 temporarily stores therein a signal calculated by the signal processor 44. The storage 46 may be, for example, a random-access memory (RAM) or a register circuit.

The coordinate extractor 45 is a logic circuit that obtains detected coordinates of the asperities of the surface of, for example, the finger Fg when the contact or the proximity of the finger Fg is detected by the signal processor 44. The coordinate extractor 45 combines the detection signals Vdet output from the respective photoelectric conversion elements PD of the sensor 10 to generate two-dimensional information representing a shape of the asperities on the surface of the finger Fg or the like or two-dimensional information representing a shape of the blood vessels in the finger Fg or the palm. The coordinate extractor 45 may output the detection signals Vdet as sensor outputs Vo instead of calculating the detected coordinates.

Figure 4:
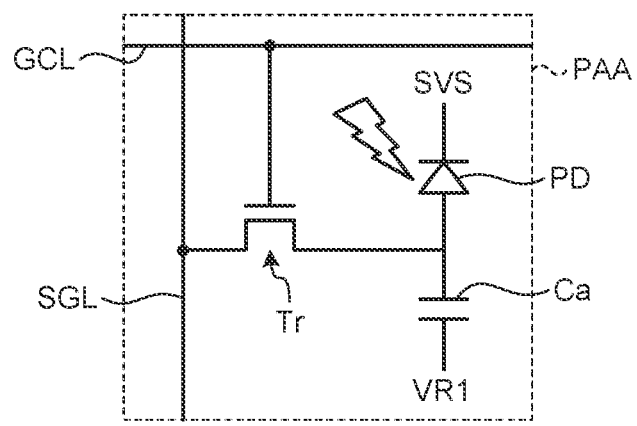
FIG. 4 is a circuit diagram illustrating a partial detection area.

The following describes a circuit configuration example and an operation example of the detection device 1. FIG. 3 is a circuit diagram illustrating the detection device. FIG. 4 is a circuit diagram illustrating a partial detection area.

As illustrated in FIG. 3, the sensor 10 has a plurality of partial detection areas PAA arranged in a matrix having a row-column configuration. As illustrated in FIG. 4, each of the partial detection areas PAA includes the photoelectric conversion element PD, a capacitive element Ca, and a first switching element Tr. The first switching element Tr is provided corresponding to each of the photoelectric conversion elements PD. The first switching element Tr includes a thin-film transistor, and in this example, includes an n-channel metal oxide semiconductor (MOS) thin-film transistor (TFT). The gate of the first switching element Tr is coupled to a corresponding one of the gate lines GCL. The source of the first switching element Tr is coupled to a corresponding one of the signal lines SGL. The drain of the first switching element Tr is coupled to the anode of the photoelectric conversion element PD and the capacitive element Ca.

The cathode of the photoelectric conversion element PD is supplied with the power supply signal SVS from the power supply circuit 103. The power supply signal SVS has a higher potential than that of the anode, and thus, the photoelectric conversion element PD is driven in a reverse bias mode. The capacitive element Ca is supplied with a reference signal VR1 serving as an initial potential of the capacitive element Ca from the power supply circuit 103.

When the partial detection area PAA is irradiated with light, a current corresponding to the amount of the light flows through the photoelectric conversion element PD. As a result, an electrical charge is stored in the capacitive element Ca. After the first switching element Tr is turned on, a current corresponding to the electrical charge stored in the capacitive element Ca flows through the signal line SGL.

The signal line SGL is coupled to the detection circuit 48 through the signal line selection circuit 16. Thus, the detection device 1 can detect a signal corresponding to the amount of the light irradiating the photoelectric conversion element PD in each of the partial detection areas PAA.

As illustrated in FIG. 3, the gate lines GCL extend in a first direction Dx and are coupled to the partial detection areas PAA arranged in the first direction Dx. A plurality of gate lines GCL1, GCL2, . . . , GCL8 are arranged in a second direction Dy and are each coupled to the gate line drive circuit 15. In the following description, the gate lines GCL1, GCL2, . . . , GCL8 will each be simply referred to as the gate line GCL when need not be distinguished from one another. The number of the gate lines GCL is eight. However, this is merely an example, and eight or more, such as 256, of the gate lines GCL may be arranged.

The first direction Dx is a direction in a plane parallel to the insulating substrate 21, and is, for example, a direction parallel to the gate line GCL. The second direction Dy is a direction in a plane parallel to the insulating substrate 21, and is a direction orthogonal to the first direction Dx. The second direction Dy may non-orthogonally intersect the first direction Dx. A third direction Dz is a direction orthogonal to the first direction Dx and the second direction Dy and is the normal direction of the insulating substrate 21. The term "plan view" refers to an arrangement relation as viewed from a direction orthogonal to a surface of the insulating substrate 21.

The signal lines SGL extend in the second direction Dy and are coupled to the partial detection areas PAA arranged in the second direction Dy. A plurality of signal lines SGL1, SGL2, . . . , SGL12 are arranged in the first direction Dx and are each coupled to the signal line selection circuit 16 and a reset circuit 17. The number of the signal lines SGL is 12. However, this is merely an example, and 12 or more, such as 252, of the signal lines SGL may be arranged.

The gate line drive circuit 15 receives the various control signals such as the start signal STV, the clock signal CK, and the reset signal RST1 through a level shifter 151. The gate line drive circuit 15 sequentially selects the gate lines GCL1, GCL2, . . . , GCL8 in a time-division manner. The gate line drive circuit 15 supplies the gate drive signals VGCL through the selected gate lines GCL to the first switching elements Tr. By this operation, the partial detection areas PAA arranged in the first direction Dx are selected as detection targets.

The signal line selection circuit 16 includes a plurality of selection signal lines Lsel, a plurality of output signal lines Lout, and third switching elements TrS. The third switching elements TrS are provided corresponding to the signal lines SGL. Six signal lines SGL1, SGL2, . . . , SGL6 are coupled to a common output signal line Lout1. Six signal lines SGL7, SGL8, . . . , SGL12 are coupled to a common output signal line Lout2. The output signal lines Lout1 and Lout2 are each coupled to the detection circuit 48.

The signal lines SGL1, SGL2, . . . , SGL6 are grouped into a first signal line block, and the signal lines SGL7, SGL8, . . . , SGL12 are grouped into a second signal line block. The selection signal lines Lsel are coupled to the respective gates of the third switching elements TrS included in one of the signal line blocks. One of the selection signal lines Lsel is coupled to the gates of the third switching elements TrS in the signal line blocks. Specifically, selection signal lines Lsel1, Lsel2, . . . , Lsel6 are coupled to the third switching elements TrS corresponding to the signal lines SGL1, SGL2, . . . , SGL6, respectively. The selection signal line Lsel1 is coupled to the third switching element TrS corresponding to the signal line SGL1 and the third switching element TrS corresponding to the signal line SGL7.

The control circuit 102 (refer to FIG. 1) sequentially supplies the selection signals SEL to the selection signal lines Lsel through level shifters 161. This operation causes the signal line selection circuit 16 to operate the third switching elements TrS to sequentially select the signal lines SGL in each of the signal line blocks in a time-division manner. With the above-described configuration, the detection device 1 can reduce the number of integrated circuits (ICs) including the detection circuit 48 or the number of terminals of the ICs.

As illustrated in FIG. 3, the reset circuit 17 includes a reference signal line Lvr, a reset signal line Lrst, and fourth switching elements TrR. The fourth switching elements TrR are provided corresponding to the signal lines SGL. The reset signal line Lrst is coupled to the gates of the fourth switching elements TrR.

The control circuit 102 supplies a reset signal RST2 to the reset signal line Lrst through a level shifter 171. This operation turns on the fourth switching elements TrR to electrically couple the signal lines SGL to the reference signal line Lvr. The power supply circuit 103 supplies the reference signal VR1 to the reference signal line Lvr. This operation supplies the reference signal VR1 to the capacitive element Ca included in each of the partial detection areas PAA.

The detection device 1 performs the detection in the order of a reset period, an exposure period, and a reading period. The power supply circuit 103 supplies the power supply signal SVS to the cathodes of the photoelectric conversion elements PD over the reset period, the exposure period, and the reading period. During the reset period, the capacitive elements Ca of all the partial detection areas PAA are sequentially electrically coupled to the signal lines SGL and are supplied with the reference signal VR1. As a result, the capacitance of the capacitive elements Ca is reset.

During the exposure period, each of the first switching elements Tr is turned off, and a current corresponding to the light irradiating the photoelectric conversion element PD flows in a corresponding one of the partial detection areas PAA. As a result, an electrical charge is stored in each of the capacitive elements Ca.

During the reading period, each of the first switching elements Tr is turned on by an operation of the gate line drive circuit 15. The control circuit 102 sequentially supplies selection signals SEL1, . . . , SEL6 to the signal line selection circuit 16. This operation sequentially or simultaneously couples the signal lines SGL of the partial detection areas PAA selected by the gate drive signals VGCL to the detection circuit 48. As a result, the detection signal Vdet is supplied to the detection circuit 48 on a partial detection area PAA basis.

The detection device 1 may perform the detection by repeating the reset period, the exposure period, and the reading period. Alternatively, the detection device 1 may start the detection operation at the time when a finger Fg or the like is detected to be in contact with or in proximity to the detection surface. In the case of a configuration in which the partial detection areas PAA are not provided with the capacitive elements Ca, the processing in the exposure period and the reading period may be performed during the same period.

Figure 5:
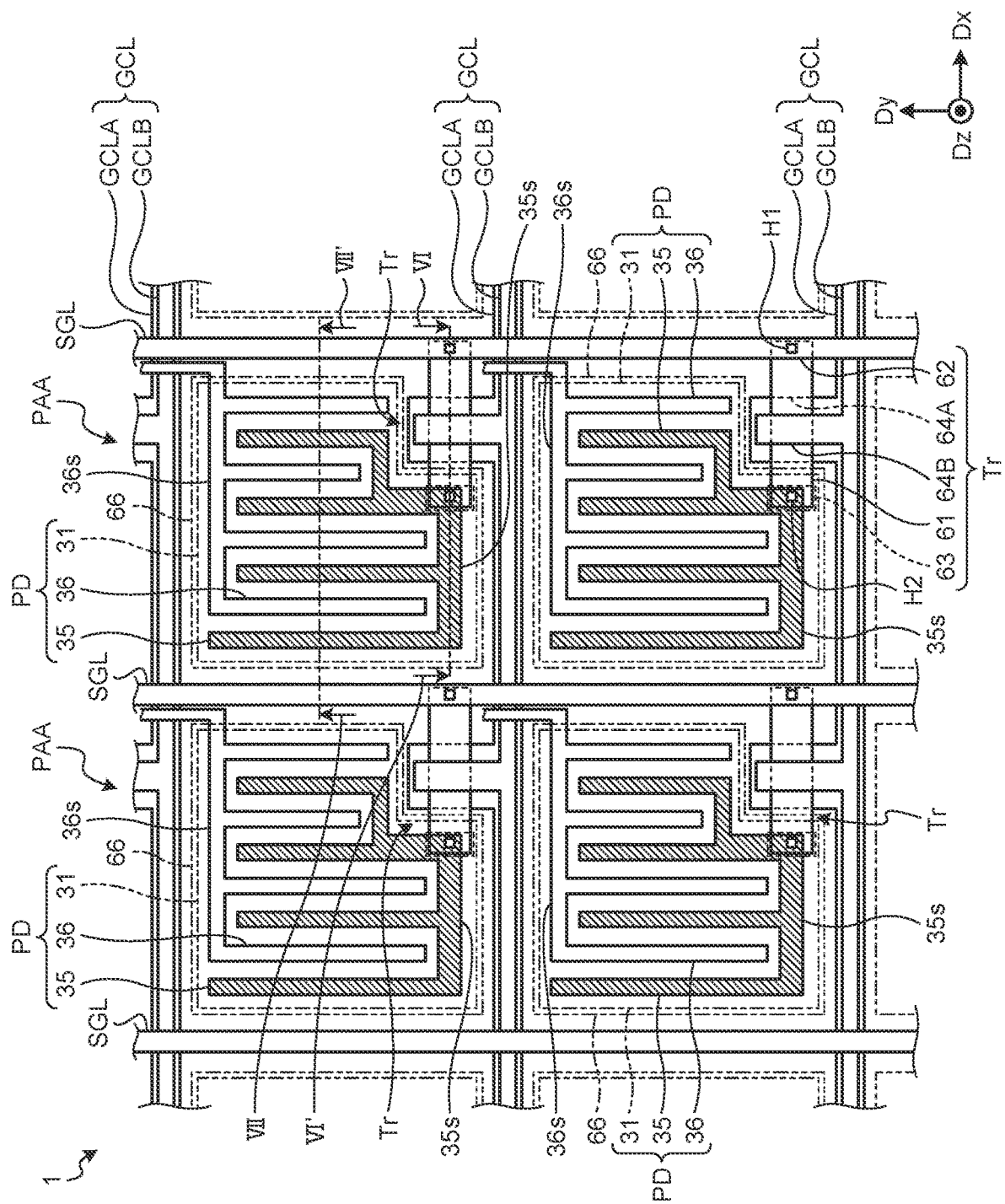
FIG. 5 is a plan view schematically illustrating the partial detection areas of the detection device according to the first embodiment.

The following describes a detailed configuration of the detection device 1. FIG. 5 is a plan view schematically illustrating the partial detection areas of the detection device according to the first embodiment. For ease of viewing, FIG.

5 illustrates the organic semiconductor layers 31 and second conductive layers 66 with long dashed double-short dashed lines. To distinguish the anode electrodes 35 from the cathode electrodes 36, the anode electrodes 35 are shaded with diagonal lines.

As illustrated in FIG. 5, the partial detection area PAA is an area surrounded by the gate lines GCL and the signal lines SGL. In the present embodiment, the gate line GCL includes a first gate line GCLA and a second gate line GCLB. The second gate line GCLB is provided so as to overlap the first gate line GCLA. The first gate line GCLA and the second gate line GCLB are provided in different layers with insulating layers (insulating layers 22c and 22d (refer to FIG. 6)) interposed therebetween. The first gate line GCLA and the second gate line GCLB are electrically coupled together at any point and are supplied with the gate drive signals VGCL having the same potential. In FIG. 5, the first gate line GCLA and the second gate line GCLB have different widths but may have the same width.

The photoelectric conversion element PD includes the anode electrodes 35, the cathode electrodes 36, and the organic semiconductor layer 31. The anode electrodes 35, the cathode electrodes 36, and the organic semiconductor layer 31 that form the photoelectric conversion element PD are provided in the area surrounded by the gate lines GCL and the signal lines SGL. That is, the photoelectric conversion elements PD (organic semiconductor layers 31) are arranged so as to be separated on a partial detection area PAA basis. In FIG. 5, for ease of viewing, each of the photoelectric conversion elements PD includes four anode electrodes 35 and four cathode electrodes 36. However, in reality, large numbers of the anode electrodes 35 and the cathode electrodes 36 are arranged.

In each of the photoelectric conversion elements PD, the anode electrodes 35 and the cathode electrodes 36 are alternately arranged in the first direction Dx, and each extend in the second direction Dy. The ends on the same side (for example, in the −Dy direction) of the anode electrodes 35 are coupled to coupling wiring 35s. With this configuration, the anode electrodes 35 are supplied with a signal that is common to the anode electrodes 35. The ends on the same side (for example, in the +Dy direction) of the cathode electrodes 36 are coupled to coupling wiring 36s. With this configuration, the cathode electrodes 36 are supplied with the power supply signal SVS as a signal that is common to the cathode electrodes 36. In this manner, the anode electrodes 35 and the cathode electrodes 36 are formed into a comb-like shape.

The anode electrodes 35 and the cathode electrodes 36 are provided so as not to overlap the first switching element Tr. Specifically, the anode electrodes 35 and the cathode electrodes 36 adjacent to the first switching element Tr in the second direction Dy are formed to have lengths in the second direction Dy less than those of the other anode electrodes 35 and the other cathode electrodes 36.

The organic semiconductor layer 31 is provided so as to cover the anode electrodes 35 and the cathode electrodes 36. With this configuration, a transverse electric field (electric field in a direction along the first direction Dx) is generated in the organic semiconductor layer 31 between each adjacent pair of the anode electrodes 35 and the cathode electrodes 36. The organic semiconductor layer 31 is provided so as to cover most of the area of the partial detection area PAA that does not overlap the first switching element Tr.

As materials of the organic semiconductor layer 31, low-molecular-weight organic materials can be used including, for example, fullerene ($C_{60}$), phenyl-$C_{61}$-butyric acid methyl ester (PCBM), copper phthalocyanine (CuPc), fluorinated copper phthalocyanine (F16CuPc), rubrene (5,6,11, 12-tetraphenyltetracene), and PDI (a derivative of perylene).

The organic semiconductor layer 31 is made using a material obtained by combining the above-listed low-molecular-weight organic materials with high-molecular-weight organic materials. As the high-molecular-weight organic materials, for example, poly(3-hexylthiophene) (P3HT) and F8-alt-benzothiadiazole (F8BT) can be used. The organic semiconductor layer 31 can be a film in the state of a mixture (having a sea-island structure) of P3HT and PCBM or a film in the state of a mixture of F8BT and PDI. A detailed configuration of the organic semiconductor layer 31 will be described later.

A metal material such as molybdenum (Mo) or aluminum (Al) is used as the anode electrodes 35 and the cathode electrodes 36. Alternatively, each of the anode electrodes 35 and the cathode electrodes 36 may be a multi-layered film obtained by stacking a plurality of these materials. The anode electrodes 35 and the cathode electrodes 36 may be formed of a light-transmitting conductive material such as indium tin oxide (ITO).

Each of the second conductive layers 66 is provided in an area overlapping the organic semiconductor layer 31 and not overlapping the first switching element Tr.

The first switching element Tr is provided near an intersection of the gate line GCL and the signal line SGL. The first switching element Tr includes a first semiconductor 61, a source electrode 62, a drain electrode 63, a first gate electrode 64A, and a second gate electrode 64B.

One end of the first semiconductor 61 is coupled to the source electrode 62 (signal line SGL) through a contact hole H1. The other end of the first semiconductor 61 is coupled to the drain electrode 63 (coupling wiring 35s) through a contact hole H2. A portion of the signal line SGL that overlaps the first semiconductor 61 is the source electrode 62. A portion of the coupling wiring 35s that overlaps the first semiconductor 61 serves as the drain electrode 63. Such a configuration allows the first switching element Tr to switch between a conductive state and a non-conductive state between the anode electrodes 35 of the photoelectric conversion element PD and the signal line SGL.

The first semiconductor 61 is an oxide semiconductor. The first semiconductor 61 is more preferably a transparent amorphous oxide semiconductor (TAOS) among oxide semiconductors. Using an oxide semiconductor as the first switching element Tr can reduce a leak current of the first switching element Tr. As a result, degradation in sensitivity in the detection device 1 can be reduced when the resolution of detection is increased. The material of the first semiconductor 61 is not limited to TAOS and may be another material such as amorphous silicon (a-Si), polysilicon, or microcrystalline silicon.

The first semiconductor 61 is provided along the first direction Dx and intersects the first gate electrode 64A and the second gate electrode 64B in the plan view. The first gate electrode 64A and the second gate electrode 64B are provided so as to branch from the first gate line GCLA and the second gate line GCLB, respectively. Aluminum (Al), copper (Cu), silver (Ag), molybdenum (Mo), or an alloy thereof is used as the first gate electrode 64A and the second gate electrode 64B. A channel area is formed at a portion of the first semiconductor 61 that overlaps the first gate electrode 64A and the second gate electrode 64B.

Figure 6:
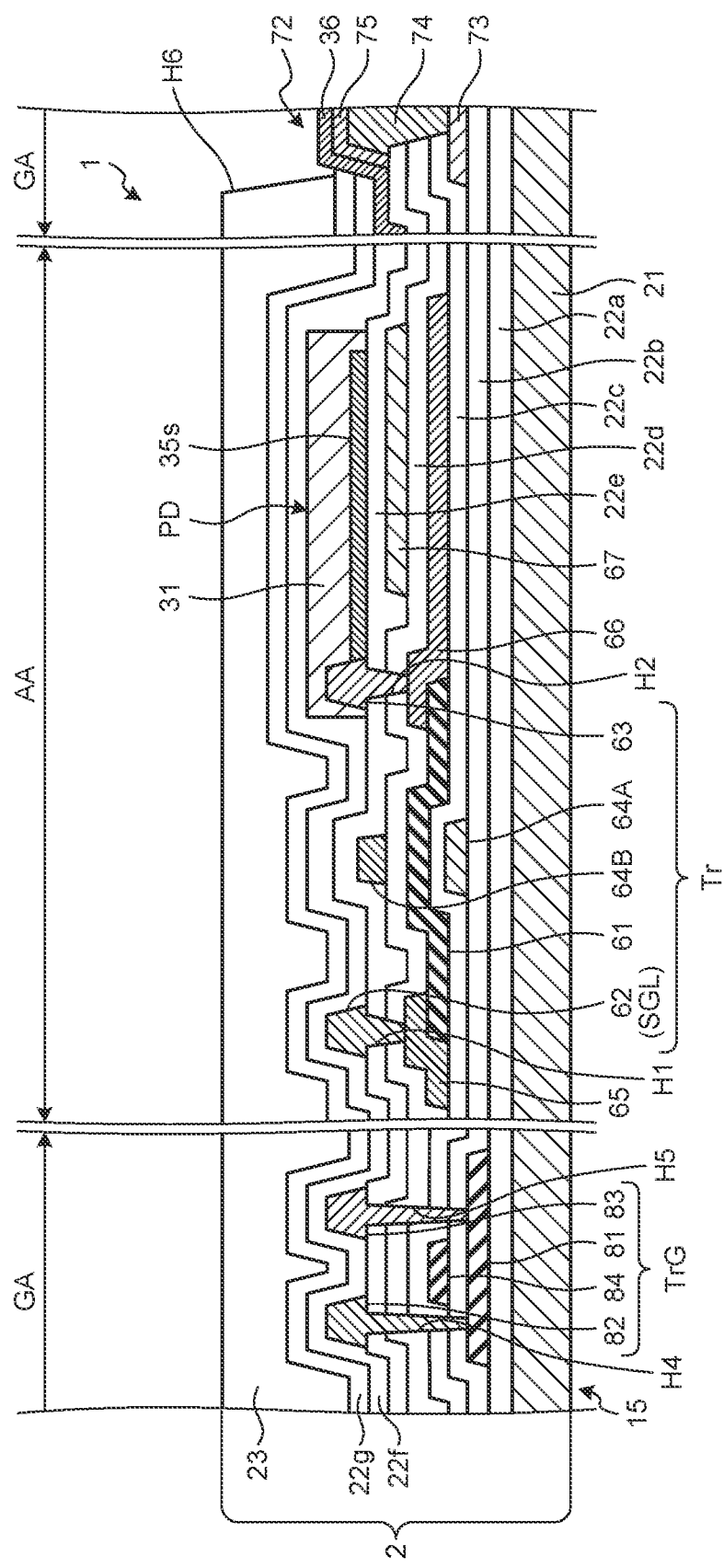
FIG. 6 is a VI-VI' sectional view of FIG. 5.

The following describes a layer configuration of the detection device 1. FIG. 6 is a VI-VI' sectional view of FIG. 5. In order to illustrate a relation between the layer structure of the detection area AA and the layer structure of the peripheral area GA, FIG. 6 illustrates a section taken along a line VI-VI' and a section of a portion of the peripheral area GA that includes a second switching element TrG, in a schematically connected manner. FIG. 6 further illustrates a section of a portion of the peripheral area GA that includes a terminal portion 72 in a schematically connected manner.

In the description of the detection device 1, a direction from the insulating substrate 21 toward an overcoat layer 23 that covers the photoelectric conversion element PD in a direction orthogonal to the surface of the insulating substrate 21 is referred to as "upper side" or simply "above". A direction from the overcoat layer 23 toward the insulating substrate 21 is referred to as "lower side" or simply "below".

As illustrated in FIG. 6, an array substrate 2 includes the insulating substrate 21, the first switching element Tr, the second switching element TrG, a first conductive layer 65, the second conductive layer 66, a third conductive layer 67, insulating layers 22a to 22g, the overcoat layer 23, various types of wiring, and the like.

The first switching element Tr is provided on the insulating substrate 21. The insulating substrate 21 is, for example, a glass substrate. Alternatively, the insulating substrate 21 may be a resin substrate or a resin film formed of a resin such as polyimide. When a resin film is used as the insulating substrate 21, the array substrate 2 can be formed into a curved surface shape, and the detection device 1 is configured as a sensor having a curved surface corresponding to the shape of the finger Fg or the palm.

The first gate electrode 64A is provided above the insulating substrate 21 with the insulating layers 22a and 22b interposed therebetween. The insulating layers 22a to 22g are inorganic insulating layers and are made using, for example, a silicon oxide (SiO) film, a silicon nitride (SiN) film, or a silicon oxynitride (SiON) film. Each of the insulating layers 22a to 22g is not limited to a single layer and may be a multilayered film.

The insulating layer 22c is provided on the upper side of the insulating layer 22b so as to cover the first gate electrode 64A. The first semiconductor 61, the first conductive layer 65 and the second conductive layer 66 are provided on the upper side of the insulating layer 22c. The first conductive layer 65 is provided so as to cover one end side of the first semiconductor 61. The second conductive layer 66 is provided so as to cover the other end side of the first semiconductor 61.

The insulating layer 22d is provided on the upper side of the insulating layer 22c so as to cover the first semiconductor 61, the first conductive layer 65, and the second conductive layer 66. The second gate electrode 64B is provided on the upper side of the insulating layer 22d. The first semiconductor 61 is provided between the first gate electrode 64A and the second gate electrode 64B in the direction orthogonal to the insulating substrate 21. That is, the first switching element Tr has what is called a dual-gate structure. However, the first switching element Tr may have a bottom-gate structure that is provided with only the first gate electrode 64A, or a top-gate structure that is provided with only the second gate electrode 64B.

The insulating layer 22e is provided on the upper side of the insulating layer 22d so as to cover the first gate electrode 64A. The source electrode 62 (signal line SGL) and the drain electrode 63 (coupling wiring 35s) are provided on the insulating layer 22e. In the present embodiment, the drain electrode 63 is the coupling wiring 35s provided above the first semiconductor 61 with the insulating layers 22d and 22e interposed therebetween.

Each of the contact holes H1 and H2 is provided passing through the insulating layers 22d and 22e. The source electrode 62 is electrically coupled to the first semiconductor 61 through the contact hole H1 and the first conductive layer 65. The drain electrode 63 is electrically coupled to the first semiconductor 61 through the contact hole H2 and the second conductive layer 66.

In the detection device 1, since the first conductive layer 65 and the second conductive layer 66 are provided, the first semiconductor 61 can be restrained from being removed by an etchant when the contact holes H1 and H2 are formed by etching. That is, in the detection device 1, the first switching element Tr in the detection area AA and the second switching element TrG in the peripheral area GA can be formed in the same process. Therefore, the manufacturing cost can be reduced.

The second conductive layer 66 extends in an area overlapping the photoelectric conversion element PD in an area not overlapping the first semiconductor 61. In the area not overlapping the first semiconductor 61, the third conductive layer 67 is provided on the upper side of the insulating layer 22d. The third conductive layer 67 is provided between the second conductive layer 66 and the photoelectric conversion element PD. This configuration generates capacitance between the second conductive layer 66 and the third conductive layer 67, and capacitance between the third conductive layer 67 and the anode and cathode electrodes 35 and 36. The capacitance generated by the second conductive layer 66, the third conductive layer 67, and the photoelectric conversion element PD serves as the capacitance of the capacitive element Ca illustrated in FIG. 4.

For example, a metal material such as aluminum (Al), copper (Cu), silver (Ag), or molybdenum (Mo), or an alloy of these metals is used as the first conductive layer 65, the second conductive layer 66, and the third conductive layer 67.

The photoelectric conversion element PD is provided on the upper side of the insulating layer 22e of an array substrate 2. The insulating layers 22f and 22g are provided on the upper side of the insulating layer 22e so as to cover the photoelectric conversion element PD and the source electrode 62. The insulating layers 22f and 22g are sealing films that protect the photoelectric conversion element PD, and restrain, for example, water from entering the organic semiconductor layer 31 from outside.

The overcoat layer 23 is provided on the upper side of the insulating layer 22g so as to cover the photoelectric conversion element PD. The overcoat layer 23 is formed of an organic insulating material and is a planarizing layer that planarizes asperities formed by the first switching element Tr, the photoelectric conversion element PD, and various types of wiring.

The second switching elements TrG included in the gate line drive circuit 15 are provided in the peripheral area GA. The second switching elements TrG are provided on the same insulating substrate 21 as that of the first switching elements Tr. The second switching element TrG includes a second semiconductor 81, a source electrode 82, a drain electrode 83, and a gate electrode 84.

The second semiconductor 81 is polysilicon. The second semiconductor 81 is more preferably made of low-temperature polysilicon, or low temperature polycrystalline silicone (hereinafter referred to as LTPS). Polysilicon has higher carrier mobility than that of a-Si. Therefore, the size of the gate line drive circuit 15 of the detection device 1 can be smaller than in the case where a-Si is used for the second switching element TrG. As a result, the area of the peripheral area GA of the detection device 1 can be reduced. However, the second semiconductor 81 is not limited to polysilicon, and may be another material.

The second semiconductor 81 is provided on the upper side of the insulating layer 22a. That is, the first semiconductor 61 of the first switching element Tr is provided in a layer different from that of the second semiconductor 81 of the second switching element TrG. However, the first switching element Tr and the second switching element TrG may be provided in the same layer.

The gate electrode 84 is provided on the upper side of the second semiconductor 81 with the insulating layer 22b interposed therebetween. The gate electrode 84 is provided in the same layer as that of the first gate electrode 64A. The second switching element TrG has what is called the top-gate structure. However, the second switching element TrG may have the dual-gate structure or the bottom-gate structure.

The source electrode 82 and the drain electrode 83 are provided on the upper side of the insulating layer 22e. The source electrode 82 and the drain electrode 83 are provided in the same layer as that of the source electrode 62 and the drain electrode 63 of the first switching element Tr. The source electrode 82 is electrically coupled to the second semiconductor 81 through a contact hole H4. The drain electrode 83 is electrically coupled to the second semiconductor 81 through a contact hole H5.

The third switching elements TrS included in the signal line selection circuit 16 and the fourth switching elements TrR included in the reset circuit 17 illustrated in FIG. 3 can each have the same configuration as that of the second switching element TrG.

The terminal portion 72 is provided in a position different from an area of the peripheral area GA that is provided with the gate line drive circuit 15. The terminal portion 72 includes a first terminal conductive layer 73, a second terminal conductive layer 74, and a third terminal conductive layer 75. The first terminal conductive layer 73 is provided in the same layer as that of the first gate electrode 64A on the upper side of the insulating layer 22b. A contact hole H6 is provided so as to pass through the insulating layer 22g and the overcoat layer 23 from the insulating layer 22c.

The second terminal conductive layer 74 and the third terminal conductive layer 75 are stacked in this order in the contact hole H6, and are electrically coupled to the first terminal conductive layer 73. At least either of the second terminal conductive layer 74 and the third terminal conductive layer 75 can be formed using the same material and the same process as those of the anode electrodes 35 and the cathode electrodes 36. The coupling wiring 36s coupled to the cathode electrodes 36 extends to the peripheral area GA and is electrically coupled to the terminal portion 72. While FIG. 6 illustrates one terminal portion 72, a plurality of the terminal portions 72 may be arranged with spacing therebetween and provided as coupling terminals to the flexible printed circuit board 71 (refer to FIG. 1) or coupling terminals to a drive IC.

Figure 7:
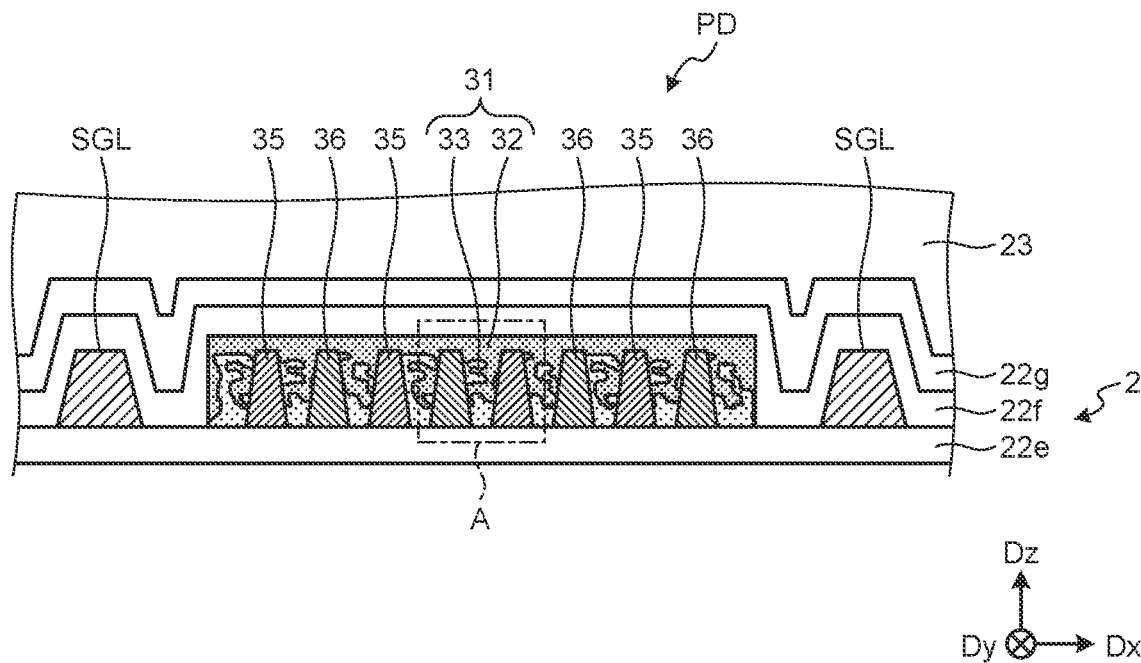
FIG. 7 is a VII-VII' sectional view of FIG. 5.
Figure 8:
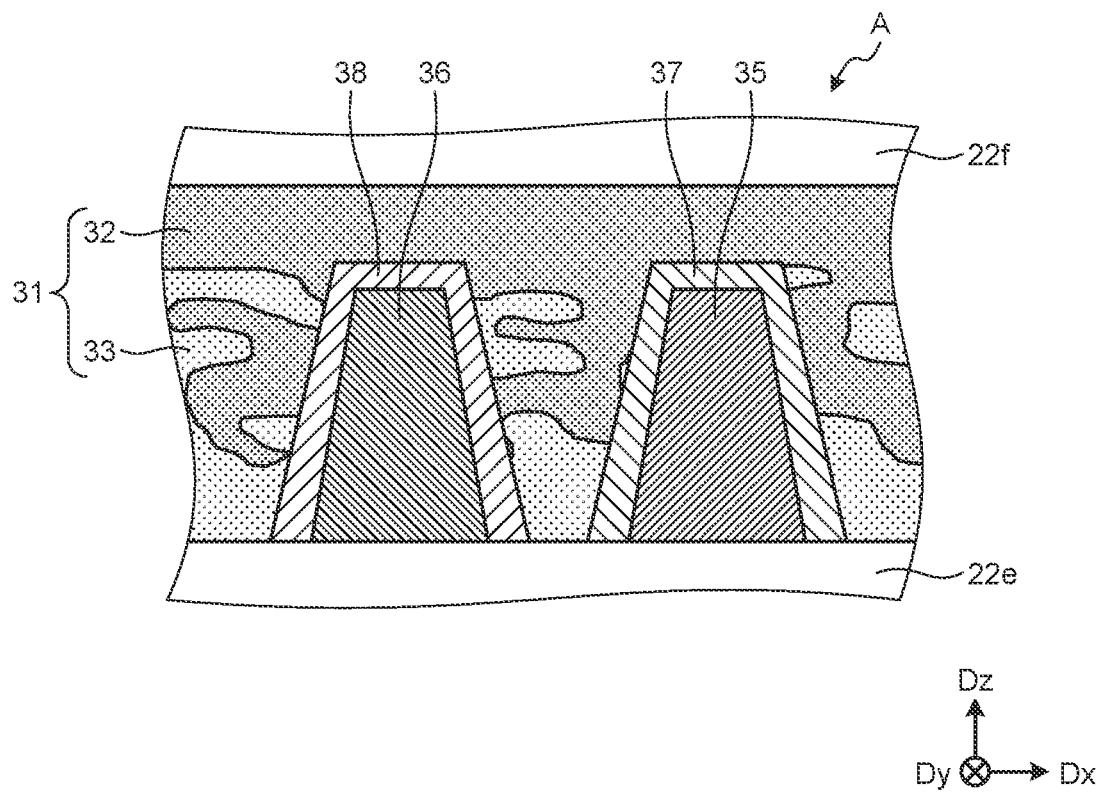
FIG. 8 is a sectional view illustrating an area A of FIG. 7 in an enlarged manner.

The following describes a sectional configuration of the photoelectric conversion element PD. FIG. 7 is a VII-VII' sectional view of FIG. 5. FIG. 8 is a sectional view illustrating an area A of FIG. 7 in an enlarged manner. FIG. 7 does not illustrate the layers below the insulating layer 22e.

As illustrated in FIG. 7, the photoelectric conversion element PD is provided between the signal lines SGL adjacent in the first direction Dx. The photoelectric conversion element PD is provided in the same layer as that of the signal lines SGL. The anode electrodes 35 and the cathode electrodes 36 are provided on the upper side of the insulating layer 22e. That is, the anode electrodes 35 and the cathode electrodes 36 are provided in the same layer in the same plane of the array substrate 2 and are arranged adjacent to each other. More specifically, a side surface of the anode electrode 35 faces a side surface of the cathode electrode 36 in the first direction Dx.

Although not illustrated in FIG. 7, the coupling wiring 35s that couples together ends of the anode electrodes 35 and the coupling wiring 36s that couples together ends of the cathode electrodes 36 are also provided on the upper side of the insulating layer 22e. However, the coupling wiring 35s and 36s are not limited to this configuration, and may be provided in a layer different from that of the anode electrodes 35 and the cathode electrodes 36 and may be electrically coupled to the anode electrodes 35 and the cathode electrodes 36 through contact holes.

The organic semiconductor layer 31 is provided on the upper side of the insulating layer 22e so as to cover the anode electrodes 35 and the cathode electrodes 36. The organic semiconductor layer 31 covers the upper and side surfaces of the anode electrodes 35, and also covers the upper and side surfaces of the cathode electrodes 36. The organic semiconductor layer 31 is provided at least between the side surfaces of the anode electrodes 35 and the side surfaces of the cathode electrodes 36 that face each other.

The thickness (height) of the organic semiconductor layer 31 is equal to or greater than, for example, approximately 500 nm. The distance between the anode electrode 35 and the cathode electrode 36 adjacent to each other is, for example, approximately 1 μm. However, for example, the shapes, the heights, and the arrangement interval of the organic semiconductor layer 31, the anode electrodes 35, and the cathode electrodes 36 are set as appropriate according to the wavelength of the light to be detected and the biological information to be detected.

The organic semiconductor layer 31 has a bulk heterostructure in which a p-type semiconductor layer 32 coexists with an n-type semiconductor layer 33. In the organic semiconductor layer 31, the p-type semiconductor layer 32 and the n-type semiconductor layer 33 are distributed at a desired ratio (for example, at a ratio of 1:2), and the density distribution gradually changes in the vertical direction.

On the lower surface side of the organic semiconductor layer 31 (near the insulating layer 22e) and on the upper surface side of the organic semiconductor layer 31 (above the anode electrodes 35 and the cathode electrodes 36), the p-type semiconductor layer 32 and the n-type semiconductor layer 33 are formed such that a relationship the p-type semiconductor layer 32>the n-type semiconductor layer 33 is satisfied and a relationship the n-type semiconductor layer 33>the p-type semiconductor layer 32 is satisfied. In the example illustrated in FIG. 8, the density distribution on the upper surface side is such that the p-type semiconductor layer 32>the n-type semiconductor layer 33, and the density distribution on the lower surface side is such that the n-type semiconductor layer 33>the p-type semiconductor layer 32. However, the density distribution of the p-type semiconductor layer 32 and the n-type semiconductor layer 33 may be reversed.

When the organic semiconductor layer 31 is irradiated with light, electron-hole pairs are generated in each of the p-type semiconductor layer 32 and the n-type semiconductor layer 33. Each of the holes and the electrons generated in the organic semiconductor layer 31 moves in the organic semiconductor layer 31 and moves in a direction (traverse direction) toward the anode electrode 35 or the cathode electrode 36.

As illustrated in FIG. 8, the anode electrode 35 is provided with a first buffer layer 37. The first buffer layer 37 covers the side and upper surfaces of the anode electrode 35 and is provided between the anode electrode 35 and the organic semiconductor layer 31. In the same manner, the cathode electrode 36 is provided with a second buffer layer 38. The second buffer layer 38 covers the side and upper surfaces of the cathode electrode 36 and is provided between the cathode electrode 36 and the organic semiconductor layer 31. The p-type semiconductor layer 32 and the n-type semiconductor layer 33 contact each of the first buffer layer 37 and the second buffer layer 38.

The first buffer layer 37 and the second buffer layer 38 are provided to facilitate the holes and the electrons generated in the organic semiconductor layer 31 to reach the anode electrode 35 or the cathode electrode 36. The first buffer layer 37 serves as an electron transport layer (or a hole blocking layer). The second buffer layer 38 serves as a hole transport layer (electron blocking layer).

For example, a titanium oxide ($TiO_x$) can be used as a material of the first buffer layer 37; and for example, tungsten oxide ($WO_3$) or yttrium oxide ($Y_2O_3$) can be used as a material of the second buffer layer 38. For example, P3HT among the above-listed organic materials is used as the p-type semiconductor layer 32. For example, PCBM among the above-listed organic materials is used as the n-type semiconductor layer 33.

Referring back to FIG. 7, the insulating layer 22f directly on the upper side of the organic semiconductor layer 31 without a conductive material such as the cathode electrode 36 interposed therebetween so as to be in contact with the organic semiconductor layer 31 and covers the organic semiconductor layer 31. The insulating layer 22f covers the entire upper surface of the organic semiconductor layer 31. The insulating layer 22g and the overcoat layer 23 are stacked in this order on the insulating layer 22f.

As described above, the detection device 1 of the present embodiment includes the insulating substrate 21 (substrate), the anode electrodes 35 provided on the insulating substrate 21, the cathode electrodes 36 that are provided in the same layer as that of the anode electrodes 35 and are located adjacent to the respective anode electrodes 35, and the organic semiconductor layer 31 that has the structure in which the p-type semiconductor layer 32 and the n-type semiconductor layer 33 coexist and that is provided so as to cover the anode electrodes 35 and the cathode electrodes 36.

With this configuration, the organic semiconductor layer 31 is driven by the transverse electric fields generated between the anode electrodes 35 and the cathode electrodes 36 provided in the same layer. Therefore, electrodes such as the anode electrodes 35 or the cathode electrodes 36 need not be provided on the upper side of the organic semiconductor layer 31. Therefore, as compared with a configuration in which electrodes are provided on the upper side of the organic semiconductor layer 31, a process such as patterning of the electrodes can be restrained from causing damage to the organic semiconductor layer 31. This can reduce degradation in detection characteristics of the photoelectric conversion element PD in the detection device 1.

Since no electrodes are provided on the upper side of the organic semiconductor layer 31, light is restrained from being reflected on the upper surface of the organic semiconductor layer 31, and thus, incident light can efficiently enter the organic semiconductor layer 31. That is, in the detection device 1, it is possible to increase the use efficiency of light.

The shapes and the arrangement of the organic semiconductor layer 31, the anode electrodes 35, and the cathode electrodes 36 are merely examples, and can be changed as appropriate. For example, the anode electrodes 35 and the cathode electrodes 36 may be provided so as to extend in a direction other than the second direction Dy. In another respect, the anode electrodes 35 and the cathode electrodes 36 are not limited to the comb-like shape and only needs to be arranged so as to form the transverse electric fields.

Second Embodiment

Figure 9:
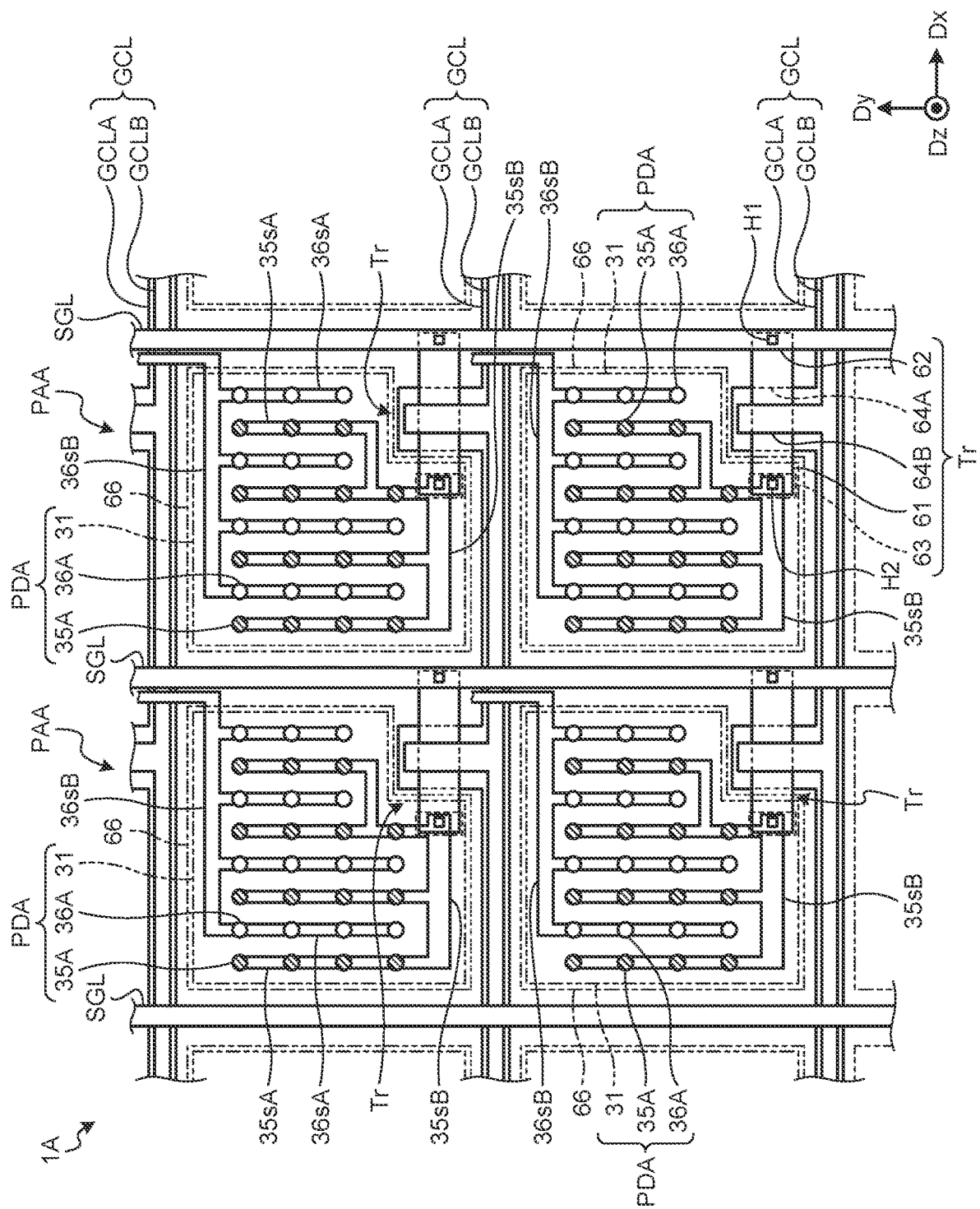
FIG. 9 is a plan view schematically illustrating the partial detection areas of a detection device according to a second embodiment.

FIG. 9 is a plan view schematically illustrating the partial detection areas of a detection device according to a second embodiment. In the following description, the same components as those described in the above-described embodiment are denoted by the same reference numerals and will not be described again.

As illustrated in FIG. 9, in a detection device 1A according to the second embodiment, photoelectric conversion elements PDA each include a plurality of cylindrical anode electrodes 35A and a plurality of cylindrical cathode electrodes 36A. The cylindrical anode electrodes 35A and the cylindrical cathode electrodes 36A are arranged in a matrix having a row-column configuration in the plan view. The anode electrodes 35A and the cathode electrodes 36A are alternately arranged at least in the first direction Dx.

The anode electrodes 35A are electrically coupled to the first switching element Tr through coupling wiring 35sA and 35sB. The cathode electrodes 36A are supplied with the power supply signal SVS through coupling wiring 36sA and 36sB. The coupling wiring 35sA and 35sB and the coupling wiring 36sA and 36sB may be provided in the same layer as that of the anode electrodes 35A and the cathode electrodes 36A, or a layer different therefrom. When the coupling wiring is provided in the different layer, the degree of freedom of arrangement of the anode electrodes 35A and the cathode electrodes 36A is improved.

Also in the present embodiment, in the same manner as in the sectional views illustrated in FIGS. 7 and 8, the anode electrodes 35A are provided in the same layer as that of the cathode electrodes 36A, and the organic semiconductor layer 31 covers the anode electrodes 35A and the cathode electrodes 36A. With this configuration, the organic semiconductor layer 31 is driven by the transverse electric fields generated between adjacent pairs of the anode electrodes 35A and the cathode electrodes 36A.

In the present embodiment, the anode electrodes 35A and the cathode electrodes 36A are cylindrical, and therefore, can have a larger surface area per unit volume. As a result, the detection characteristics of the detection device 1A can be improved.

The above-described detection devices 1 and 1A are not limited to being used in a stand-alone manner but may have a display panel or a touchscreen stacked thereon. In this case, the detection devices 1 and 1A may use light from the display panel to detect the biological information or may include a light source separately from the display panel.

While the preferred embodiments of the present disclosure have been described above, the present disclosure is not limited to the embodiments described above. The content disclosed in the embodiments is merely an example, and can be variously modified within the scope not departing from the gist of the present disclosure. Any modification appropriately made within the scope not departing from the gist of the present disclosure also naturally belongs to the technical scope of the present disclosure.

What is claimed is:

1. A detection device comprising:
   a substrate;
   an anode electrode provided on the substrate;
   a cathode electrode that is provided on the same layer as that of the anode electrode and is adjacent to the anode electrode; and
   an organic semiconductor layer that has a structure in which a p-type semiconductor layer and an n-type semiconductor layer coexist and that is provided so as to cover the anode electrode and the cathode electrode, wherein
   the organic semiconductor layer covers both side surfaces and a top surface of the anode electrode and both side surfaces and a top surface of the cathode electrode.

2. The detection device according to claim 1, comprising a plurality of the anode electrodes and a plurality of the cathode electrodes, wherein
   the anode electrodes and the cathode electrodes are alternately arranged in a first direction and each extend in a second direction intersecting the first direction.

3. The detection device according to claim 1, comprising:
   a first buffer layer that covers the anode electrode and is provided between the anode electrode and the organic semiconductor layer; and
   a second buffer layer that covers the cathode electrode and is provided between the cathode electrode and the organic semiconductor layer.

4. The detection device according to claim 1, comprising an inorganic insulating layer that is provided on an upper side of the organic semiconductor layer so as to be in contact with the organic semiconductor layer and covers the organic semiconductor layer.

5. The detection device according to claim 1, comprising a plurality of photoelectric conversion elements arranged on the substrate, wherein
   each of the photoelectric conversion elements is provided with a plurality of the anode electrodes, a plurality of the cathode electrodes, and the organic semiconductor layer.

6. The detection device according to claim 5, comprising:
   a plurality of switching elements corresponding to the photoelectric conversion elements;
   a plurality of gate lines; and
   a plurality of signal lines, wherein
   the anode electrodes, the cathode electrodes, and the organic semiconductor layer are provided in an area surrounded by the gate lines and the signal lines.

* * * * *